United States Patent [19]
Shutt

[11] Patent Number: 5,292,330
[45] Date of Patent: Mar. 8, 1994

[54] RETRACTABLE SURGICAL INSTRUMENT WITH CURVED OPERATIVE ELEMENT

[75] Inventor: George V. Shutt, Glendora, Calif.

[73] Assignee: Linvatec Corporation, Largo, Fla.

[21] Appl. No.: 829,602

[22] Filed: Jan. 29, 1992

Related U.S. Application Data

[63] Continuation of Ser. No. 531,176, May 31, 1990, abandoned.

[51] Int. Cl.$^5$ .............................................. A61B 17/32
[52] U.S. Cl. ...................................... 606/170; 606/167
[58] Field of Search ............... 606/167, 170, 171, 172, 606/160, 79, 206, 185, 46, 47; 30/162, 286

[56] References Cited

U.S. PATENT DOCUMENTS

| | | | |
|---|---|---|---|
| 1,274,669 | 8/1918 | Bohn | 606/206 |
| 1,294,284 | 2/1919 | Logeman | 606/206 X |
| 3,404,677 | 10/1968 | Springer | 606/206 X |
| 3,522,809 | 8/1970 | Cornell | 606/172 X |
| 4,174,715 | 11/1979 | Hasson | 606/206 |
| 4,294,254 | 10/1981 | Chamness | 606/47 |
| 4,427,014 | 1/1984 | Bel et al. | 606/206 X |
| 4,444,184 | 4/1984 | Oretorp | 606/79 |
| 4,474,174 | 10/1984 | Petruzzi | 606/46 X |
| 4,512,344 | 4/1985 | Barber | 606/170 X |
| 4,674,500 | 6/1987 | De Satnick | 30/286 X |
| 4,726,370 | 2/1988 | Karasawa et al. | 606/46 |
| 4,739,760 | 4/1988 | Chin et al. | 606/171 X |
| 4,840,176 | 6/1989 | Ohno | 606/47 |
| 4,926,877 | 5/1990 | Bookwalter | 606/185 X |
| 4,931,059 | 6/1990 | Markham | 606/185 |
| 4,994,079 | 2/1991 | Genese et al. | 606/206 |

FOREIGN PATENT DOCUMENTS

| | | | |
|---|---|---|---|
| 2748057 | 5/1979 | Fed. Rep. of Germany | 606/170 |
| 3231127 | 2/1984 | Fed. Rep. of Germany | 606/170 |
| 1452185 | 10/1976 | United Kingdom | 606/206 |

*Primary Examiner*—Michael H. Thaler
*Attorney, Agent, or Firm*—Gene Warzecha

[57] ABSTRACT

A retractable surgical instrument having a transversely preformed, curved operative element extendible from a straight, linear sheath. The operative element is retained in the retracted position until the distal tip of the instrument has been positioned at a work site. Cutting edges on the curved operative element may be formed in a variety of styles, one such style being embodied as an arthroscopic knife wherein the tip of the knife blade is preformed such that it maintains a transverse curve when it is extended to an operating position. The cutting edges of the transverse knife blade may extend longitudinally from the protective sheath in which case the edges are spaced from the inside surfaces of the linear sheath by the cooperative action of a raised bearing surface on the knife and the edge of the sheath adjacent the concave side of the curve as well as by laterally extending edge protection projections.

5 Claims, 6 Drawing Sheets

RETRACTABLE SURGICAL INSTRUMENT WITH CURVED OPERATIVE ELEMENT

This is a continuation of application Ser. No. 07/531,176, filed May 31, 1990, now abandoned.

BACKGROUND OF THE INVENTION

1. Field of the Invention

The invention relates generally to retractable devices which have an operating element movable between an exposed, working position and a covered, storage position. More particularly, the invention relates to manually operable retractable surgical devices which have uniquely shaped operative elements capable of being extended from a retracted position to a selected extended position.

2. Description of the Prior Art

Retractable cutting devices for use in surgical procedures are commonly known in the prior art. The retractable nature of such devices assures that the working or cutting surface of the instrument will be held retracted within the device in such a way as to not interfere with the placement of the device at the work site to be operated upon. Very often the working or operative portion of the instrument is at the distal end of a generally longitudinal support member. When the distal end has been moved past or through areas which are interposed between the entry point of the instrument and the work site, the operative portion of the instrument, often a cutting surface, may be extended from its protective sheath in order to perform the desired surgical procedure without unintentionally injuring surrounding tissue.

The present invention is particularly adaptable to small cutting instruments and is, therefore, intended primarily for use in arthroscopy or microsurgery of the knee and other joints in humans (or other animals). Consequently, for explanatory purposes, the invention will be described in terms of an arthroscopic knife. It will be understood, however, that the principles of this invention are equally applicable to other surgical, and even non-surgical, cutting and non-cutting devices. For these reasons, the disclosed preferred embodiment of the invention and the use herein of terms such as "knife", "cutting", "blades" and the like should not be considered as limiting the scope of the invention.

Arthroscopy involves the use of viewing, probing and cutting devices that can be utilized through a very small opening in the patient's skin. The procedure necessarily involves the steps of insertion, retraction and manipulation of various instruments or devices through the skin to an area to be operated upon. Such steps are primarily blind until the device comes into view of the arthroscope positioned at the work site through another opening. Consequently, it is desirable that any cutting or other potentially dangerous instruments be protected from either unintentionally injuring the patient or from being damaged by other tools during the blind maneuvers. Retractable cutting devices are obviously quite desirable in arthroscopic procedures.

In addition to the desirability of retractable devices, it should be apparent that numerous shapes of operating elements are desirable. Surgical and other operating elements may obviously be provided with a variety of different profiles suitable for different tasks. In arthroscopic applications, for example, it is often desirable to have a surgical element curved in a plane transverse to the blade plane, such a shape being more suitable for certain procedures than a straight single or double-edge knife. Prior art arthroscopic knives are known which have transversely curved cutting edges wherein the curve of the cutting blade is established and guided by the curve of the flattened, curved guide sheath situated at the distal end of the instrument and within which the blade reciprocates between a retracted and an extended position. Known examples of such curved surgical instruments are the 3M Sheathed Knives available from the Orthopedic Products Division of the Minnesota Mining and Manufacturing Company.

One disadvantage associated with instruments having a blade reciprocable within a transversely curved sheath is that it is more difficult to insert such instruments into the desired work site. The curved sheath must be manipulated through what is essentially a straight longitudinal bore previously formed in the tissue by an arthroscopic obturator or trocar. This must be done with extreme care to avoid injuring portions of the body or joint interposed between the entry point of the instrument and the work site. Moreover, in some instances the surgeon may choose to utilize a rigid cannula or portal through which the instruments must be inserted. In these cases use of a curved sheath is impossible.

One of the concerns that must be addressed in all reciprocable cutting instruments is that the cutting edges of the operative element must be somehow spaced from adjacent surfaces of the protective sheath in order to prevent the cutting edges from being dulled during the extension and/or retraction of the element.

In view of the above, it is an object of this invention to provide a retractable surgical instrument having a curved operative element encased within a linear sheath.

It is also an object of this invention to provide a retractable surgical instrument having a curved operative element encased within a flattened linear sheath.

It is another object of this invention to provide a retractable surgical instrument having a curved operative element encased within a distally located, flattened linear sheath wherein the cutting edges of the element are spaced from the inside surfaces of the sheath during extension and/or retraction of the element.

It is still another object of this invention to provide a retractable surgical instrument having a curved operative element encased within a distally located, flattened linear sheath wherein an indication is provided at the distal tip of the instrument of the direction of curvature of the element.

It is yet another object of this invention to provide a retractable surgical instrument having a curved operative element encased within a flattened linear sheath wherein the curve of the element is such that the distal tip of the element will, in an extended position be situated beyond the plane of either broad side of the flattened sheath.

SUMMARY OF THE INVENTION

These and other objects of the invention are achieved by the preferred embodiment disclosed herein which is a retractable surgical instrument comprising: a handle; an elongated tubular member secured to and extending from said handle; an elongated, longitudinally movable support shaft aligned within said tubular member, said support shaft having a proximal end thereof extending rearwardly of said tubular member into said handle; an operative surgical element secured to the distal end of said support shaft and movable therewith between a retracted position, wherein said element is enclosed within said tubular member, and at least one extended position, wherein said element is extended from said tubular member, said element preformed to maintain a transverse curve when in said extended position; and trigger means operatively situated on said handle for extending and retracting said element, said trigger means operable upon the proximal end of said support shaft to thereby move said element between said retracted and extended positions.

The invention may be embodied in a surgical instrument as described above wherein the surgical element is a flattened, transversely curved knife blade having a predetermined length and having a cutting edge over at least a portion of the edge of the blade and further comprising a linearly extending raised bearing surface on the concave side of the curve, the bearing surface cooperating with a portion of the tubular member to maintain the cutting edges of the element spaced from the interior of the tubular member.

DESCRIPTION OF THE PREFERRED EMBODIMENT

Figure 1:
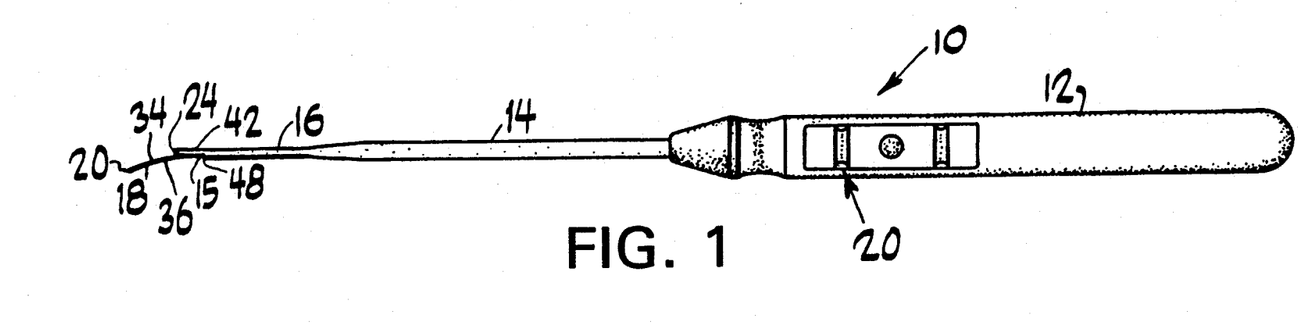
FIG. 1 shows a side elevational view of a surgical instrument constructed in accordance with the principles of this invention.
Figure 2:
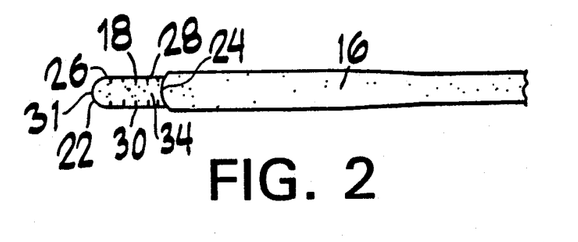
FIG. 2 shows a top plan elevational view of the distal portion of the instrument shown in FIG. 1.
Figure 3:
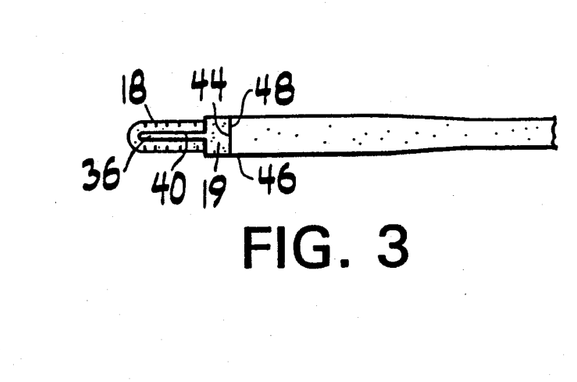
FIG. 3 shows a bottom plan elevational view of the distal portion of the instrument shown in FIG. 1.

Referring to the drawings, FIG. 1 shows a side elevational view of a retractable arthroscopic surgical instrument 10 constructed in accordance with the principles of this invention. Instrument 10 includes a handle 12, a tubular member 14 extending from one end of the handle and having a slit opening 15, a flattened and broadened protective sheath portion 16 at the distal end of tubular member 14 and an operative surgical element 18. FIGS. 2 and 3 show top and bottom plan views of the distal portion of FIG. 1, respectively. Each of the FIGS. 1, 2, and 3 show a particular type of operative element 18 in an extended position.

For explanatory purposes, the invention will be described in terms of element 18 but it will be understood by those skilled in the art that many different types of operative elements may be incorporated into the invention disclosed herein. Some of the different elements are shown in FIGS. 5 to 11.

It will be understood that element 18 may be placed in an extended position as shown or in a retracted position wherein the element is retracted by moving manual slide trigger 20 rearwardly such that the distal tip 22 of element 18 is placed behind distal tip 24 of sheath 16. While the present invention is not concerned with the particular operating mechanism of trigger 20, one example of a suitable operating mechanism is disclosed in co-pending U.S. application Ser. No. 07/465,673, now Pat. No. 5,141,517, filed Jan. 16, 1990, entitled "Retractable Instrument" and assigned to the assignee hereof. It should be understood that the present invention is adaptable to a variety of trigger operating (i.e. advancing and retracting) mechanisms.

Figure 4:
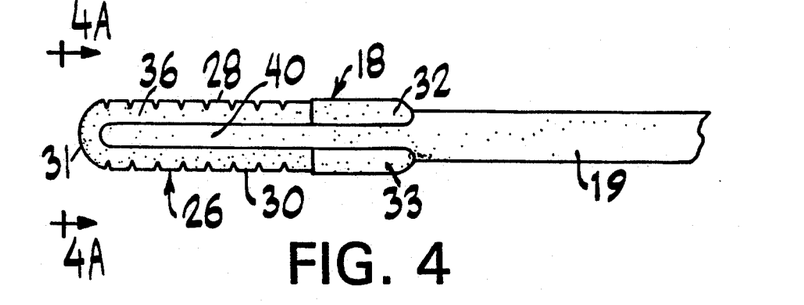
FIG. 4 is an exploded view of the distal cutting tip of the instrument shown in FIG. 3 but without the protective sheath.

Operative element 18 is integrally formed with support shaft 19 (only a portion of which is shown in FIG. 3) extending through tubular member 14 and ultimately operatively connected to trigger means 20. While support shaft 19 should be straight in order to conform to the shape of tubular member 14, operative element 18 is preformed so that in an extended position it will curve transversely to the axis of the instrument and the body of the element, as best seen in FIG. 1. It will be understood that the integral and preformed nature of element 18 also exists in the numerous other types of operative elements shown in FIGS. 5 through 11. In the embodiment of FIG. 4, element 18 is a flattened knife which is side-sharpened on one side and has a U-shaped cutting edge 26 having two straight serrated sides 28 and 30 and a curved distal tip 31. The distance between sides 28 and 30 is slightly less than the distance between the outermost lateral sides of edge protection projections 32 and 33 in order to keep cutting edges 28 and 30 laterally spaced from the narrow sides of the flattened sheath. The spacing of the cutting edges from adjacent surfaces maintains the sharpness of the edges. Operative element 18 has a flattened rear surface 34 and a profiled front surface 36, the latter including a raised, longitudinally extending bearing surface 40 which, in the preferred embodiment is an extension of one side of shaft 19. The inside edge 48 of slit opening 15 bears against bearing surface 40 upon retraction of element 18, thereby straightening the element out sufficiently to enable its retraction into sheath 16 while also transversely spacing cutting edge 26 from the adjacent interior surfaces of sheath 16. As will be seen in FIG. 12, in some instances a longitudinally extending ridge will also help to transversely space the curved operative element.

The distal tip of sheath 16 is provided with a guard projection 42 which, in the preferred embodiment, is an extension of one broad side of sheath 16. If the sheath is not flattened as shown, some other suitable guard projection may be provided, the purpose being to cover the distal tip of element 18 and to provide a smoothly contoured distal tip for tubular member 14 to facilitate insertion into a patient. In the preferred embodiment, sheath 16 is cut away at 44 on the concave side of the curve of the blade to thereby produce guard projection 42 and to provide a curve indicator or window 46 so that the surgeon will know the direction in which the curve of the blade will be directed upon extension. It will be understood by those skilled in the art that the curve of element 18 should be within a predetermined range in order to enable its extension and retraction without destroying the preformed curve. In any event, it is desirable for the curve to be great enough to have the distal tip of element 18 lie outside the plane of flattened sheath 16 (best seen in FIG. 1).

Figure 4A:
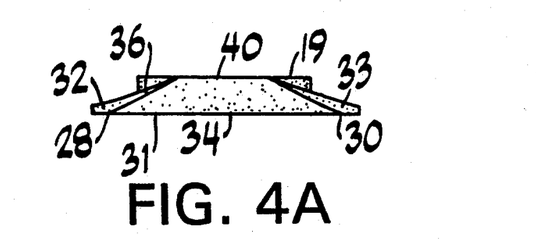
FIG. 4A is a diagrammatic end view of FIG. 4 taken along lines 4A—4A.
Figure 4B:
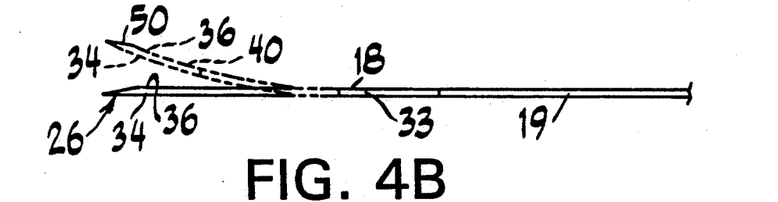
FIG. 4B is a diagrammatic side elevational view of FIG. 4 showing the distal cutting tip of FIG. 4 in a straight configuration (solid line) and one alternate, curved configuration (phantom lines).

FIG. 4B shows a diagrammatic side elevational view of the surgical element 18 of FIG. 4. It is clear in this view that cutting edge 26 is formed by sharpening only one side of the distal tip of element 18. That is, in the transverse direction, as better seen in FIG. 12 distal tip 50 has an unsymmetrical shape relative to the axis of the distal tip of element 18. It will be understood that this type of configuration inherently produces the longitudinally extending bearing surface 40 (merely by not grinding that portion of support shaft 19). When element 18 is curved upwardly as seen in FIG. 4B, bearing surface 40 will be on the upper concave side of the upwardly extending phantom line drawing. This upwardly extending line shows element 18 with a left curve (i.e. that which is shown in FIGS. 1 and 3, the directions left and right being determined relative to trigger 20 which is intended to be thumb-operated).

Figure 5:
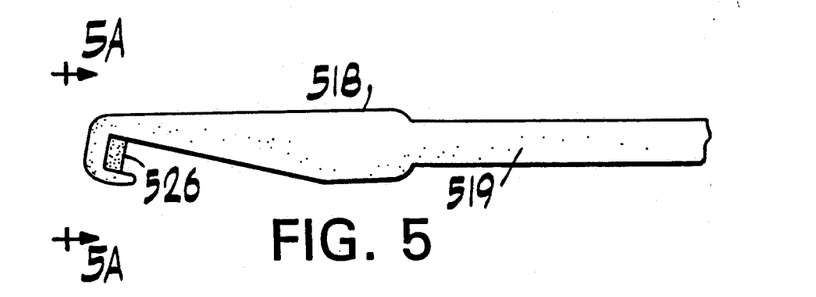
FIG. 5 is a diagrammatic plan view of an alternate embodiment of the distal cutting tip of the instrument.
Figure 5A:
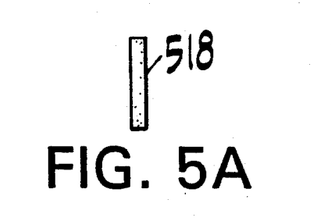
FIG. 5A is an end view taken along the lines 5A—5A of FIG. 5.

FIGS. 5 through 11 show alternate shapes of surgical elements integrally formed into support shaft 19. FIGS. 5A through 11A show the corresponding end views of each of the embodiments in FIGS. 5 through 11, respectively. Similarly, FIGS. 5B through 11B show diagrammatic straight, left and right curve configurations of the embodiments shown in FIGS. 5 through 11, respectively. In each of these drawings, the elements shown in FIGS. 4, 4A and 4B have been comparably numbered with the prefix of the particular drawing number. Thus, the operative surgical element shown in FIG. 5 is numbered 518, the support shaft is numbered 518 and the cutting edge is numbered 526. It will be noted that none of the embodiments shown in FIGS. 5 through 11 incorporate a defined area like longitudinal bearing surface 40 which is used in the embodiment of FIG. 4 to protect cutting edge 26 and keep it spaced from edge 48 as the element is retracted and extended from a sheath. The protection function served by bearing surface 40 is provided by the broad, flat sides of cutting elements 518, 618, 718, 818, 918, 1018 and 1118. In all of these embodiments, the respective cutting edges may be sharpened on both sides to provide a forwardly extending symmetrical point as best seen in FIGS. 6A, 7A, 10A and 12 without the necessity for any separately defined bearing surface. In effect, the entire surface of one flat side of these various cutting elements serves as a spacing bearing surface when the elements are curved.

Figure 5B:
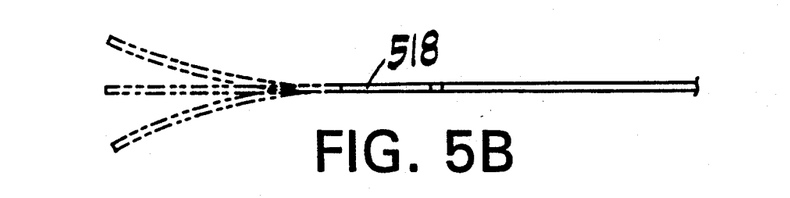
FIG. 5B is a diagrammatic side elevational view showing straight and curved configurations of the cutting tip of FIG. 5.
Figure 6:
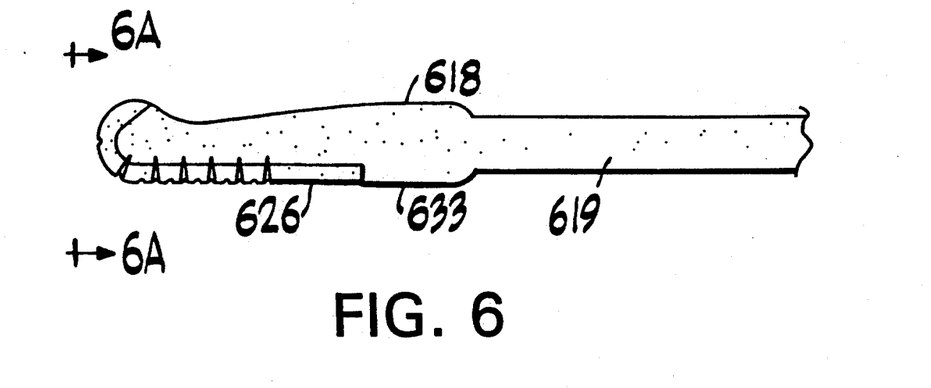
FIG. 6 is a diagrammatic plan view of an alternate embodiment of the distal cutting tip of the instrument.
Figure 6A:
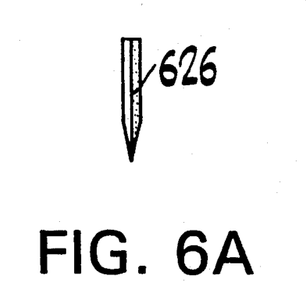
FIG. 6A is an end view taken along the lines 6A—6A of FIG. 6.
Figure 6B:
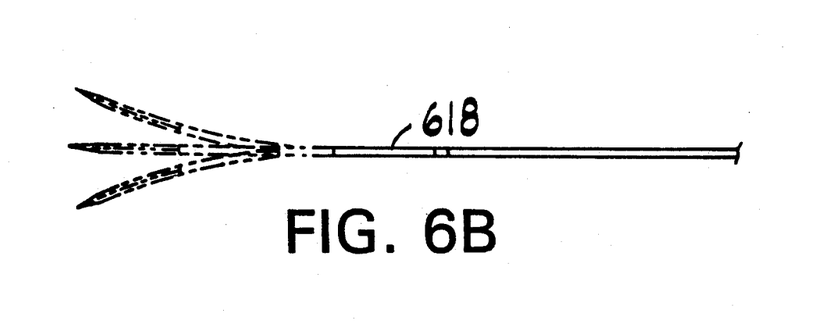
FIG. 6B is a diagrammatic side elevational view showing straight and curved configurations of the cutting tip of FIG. 6.
Figure 7:
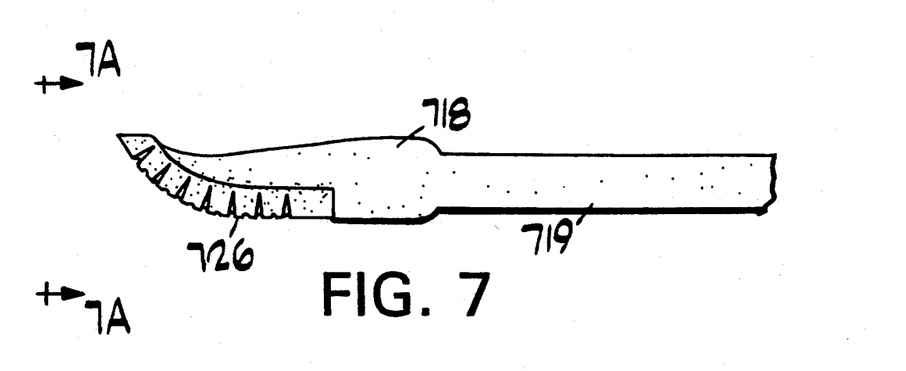
FIG. 7 is a diagrammatic plan view of an alternate embodiment of the distal cutting tip of the instrument.
Figure 7A:
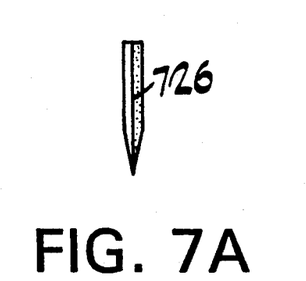
FIG. 7A is an end view taken along the lines 7A—7A of FIG. 7.
Figure 7B:
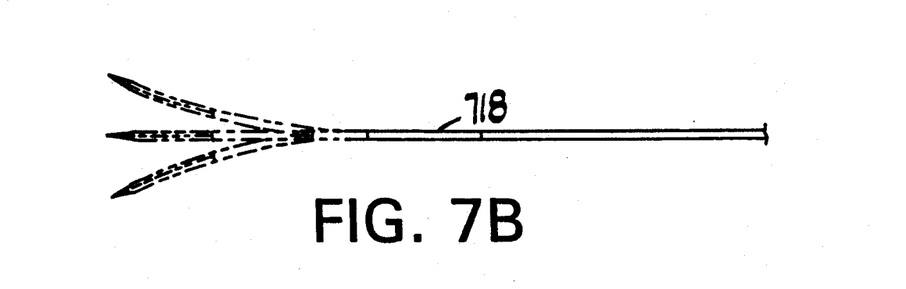
FIG. 7B is a diagrammatic side elevational view showing straight and curved configurations of the cutting tip of FIG. 7.
Figure 8:
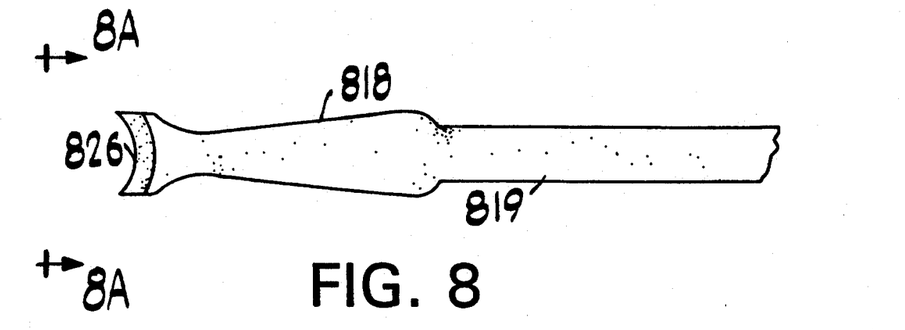
FIG. 8 is a diagrammatic plan view of an alternate embodiment of the distal cutting tip of the instrument.
Figure 8A:
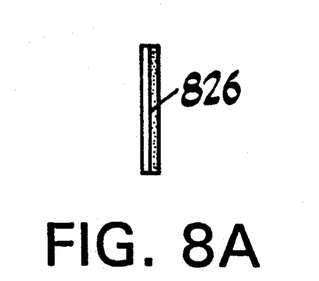
FIG. 8A is an end view taken along the lines 8A—8A of FIG. 8.
Figure 8B:
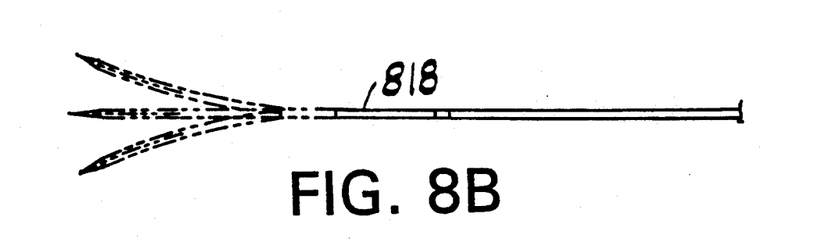
FIG. 8B is a diagrammatic side elevational view showing straight and curved configurations of the cutting tip of FIG. 8.
Figure 9:
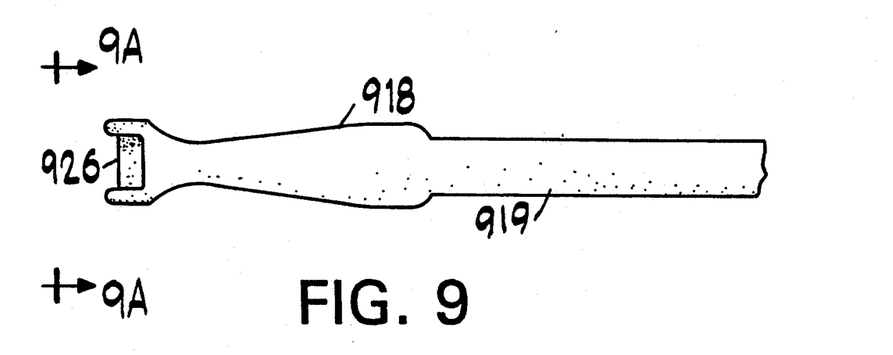
FIG. 9 is a diagrammatic plan view of an alternate embodiment of the distal cutting tip of the instrument.
Figure 9A:
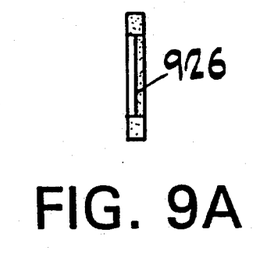
FIG. 9A is an end view taken along the lines 9A—9A of FIG. 9.
Figure 9B:
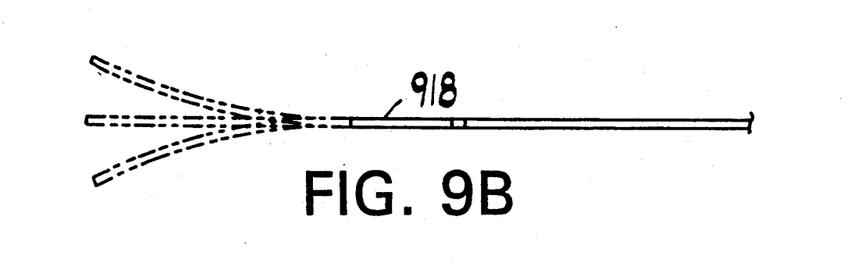
FIG. 9B is a diagrammatic side elevational view showing straight and curved configurations of the cutting tip of FIG. 9.
Figure 10:
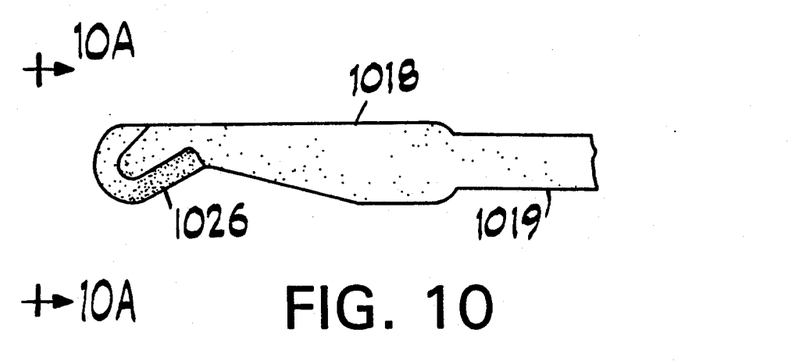
FIG. 10 is a diagrammatic plan view of an alternate embodiment of the distal cutting tip of the instrument.
Figure 10A:
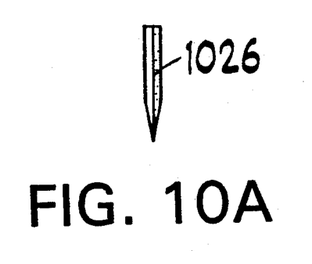
FIG. 10A is an end view taken along the lines 10A—10A of FIG. 10.
Figure 10B:
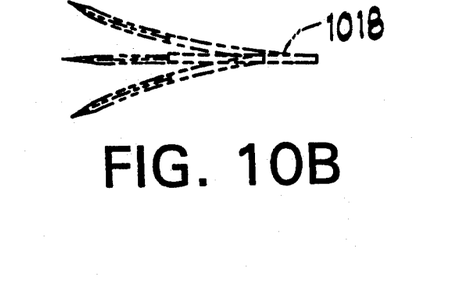
FIG. 10B is a diagrammatic side elevational view showing straight and curved configurations of the cutting tip of FIG. 10.
Figure 11:
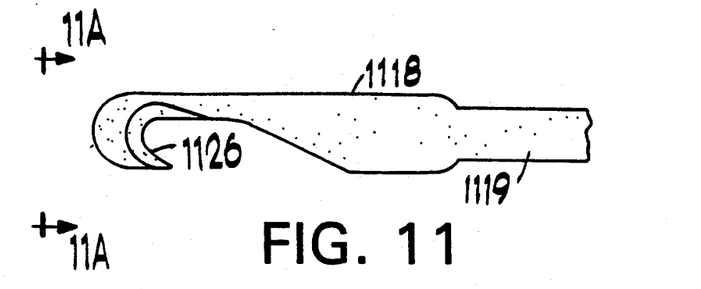
FIG. 11 is a diagrammatic plan view of an alternate embodiment of the distal cutting tip of the instrument.
Figure 11A:
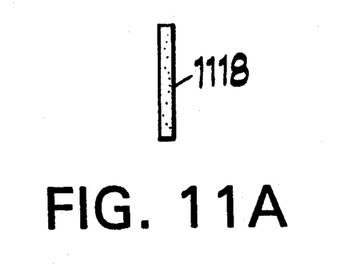
FIG. 11A is an end view taken along the lines 11A—11A of FIG. 11.
Figure 11B:
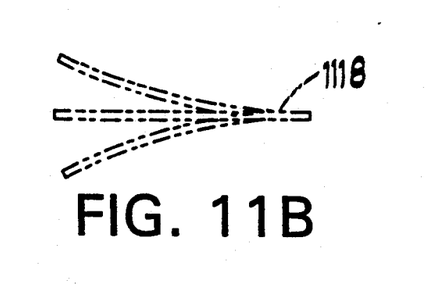
FIG. 11B is a diagrammatic side elevational view showing straight and curved configurations of the cutting tip of FIG. 11.

The side elevational views of these various embodiments are shown to demonstrate the various cutting edges available with each element and to demonstrate that each element may be made in a variety of straight or transversely preformed curve configurations. The embodiments shown in FIGS. 5B and 11B show that the inwardly facing cutting edges 526 and 1126 appear squared off in the side elevational views because the respective edges 526 and 1126 face inwardly (i.e. proximally). The embodiment of FIG. 9B appears squared off in side elevational view because the cutting edge 926 is protected on either side by extensions of the lateral surfaces of the body of element 918.

Figure 12:
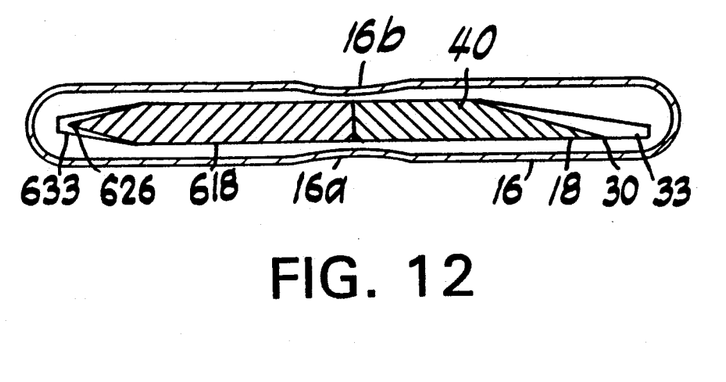
FIG. 12 is a two-part diagrammatic cross-sectional view of a surgical instrument showing the protective sheath in relation to a center-sharpened type cutting edge (left side) and a side sharpened type edge (right side).

FIG. 12 diagrammatically shows the relationship between a particular operative element and the sheath 16. For explanatory purposes, FIG. 12 represents a cross-sectional view of sheath 16 and has been divided into a left side showing the cross-section of a representative center-sharpened operative element such as element 618 (best seen in FIG. 6) and a right side showing a representative view of a side-sharpened operative element such as element 18 (best seen in FIGS. 1 through 4). It will be noted that the cutting edge 626 of element 618 is protected by an edge protection projection 633 which extends laterally beyond cutting edge 626. Similarly, cutting edge 30 of element 18 is protected by a laterally extending edge protection projection 33. In each instance, edge protection projections 633 and 33 are formed by grinding or etching the main support shaft of the operative element to a lesser degree than that which is required to form cutting edge 626 or 30, respectively.

Sheath 16 is, in some instances, formed with longitudinally extending and inwardly projecting ridges 16A and 16B which may be inherently formed during the process by which the flattened sheath 16 is formed from round stock. These inwardly projecting ridges act as additional bearing surfaces which aid in operation of the device by making the extension and retraction of the operative elements easier.

It will be understood by those skilled in the art that numerous other modifications and improvements may be made to the preferred embodiment of the invention disclosed herein without departing from the spirit and scope thereof.

What is claimed is:

1. A retractable surgical instrument comprising:
   a handle;
   an elongated tubular member secured to and extending from said handle, said tubular member being cylindrical and having its distal end formed into a flattened linear sheath terminating in a slit opening;
   an elongated, longitudinally movable support shaft aligned within said tubular member, said support shaft having a proximal end thereof extending rearwardly of said tubular member into said handle;
   an operative surgical element secured to the distal end of said support shaft and movable therewith between a retracted position, wherein said element is enclosed within said tubular member, and at least one extended position, wherein said element is extended from said tubular member, said element preformed to maintain a predetermined transverse curve when in said extended position;
   a guard projection extending a predetermined distance from the distal end of only one side of said flattened sheath, said element having its concave side facing away from said guard projection when it is extended from said sheath; and
   trigger means operatively situated on said handle for extending and retracting said element, said trigger means operable upon the proximal end of said support shaft to thereby move said element between said retracted and extended positions.

2. A retractable surgical instrument according to claim 1 wherein said surgical element comprises a cutting edge over at least a portion thereof and further comprising an axially extending bearing surface on the concave side of said transverse curve, said bearing surface transversely spaced from said cutting edge and cooperating with an adjacent portion of the interior surface of said tubular member to maintain said cutting edge of said element transversely spaced from the interior surface of said tubular member.

3. A retractable surgical element according to claim 2 wherein said support shaft has a proximal portion of a predetermined thickness situated contiguously and proximally to said surgical element and wherein said bearing surface is an integral extension of said proximal portion of said support shaft.

4. A retractable surgical instrument according to claim 1 wherein said guard projection has a width substantially equal to or greater than that of said surgical element and a distal tip contoured to facilitate passage of said tip through an area interposed between a first point where said instrument is introduced into a body to be worked upon and a second point where said element is to be extended from said tubular member.

5. A retractable surgical instrument according to claim 1 wherein said operative surgical element comprises at least one longitudinally extending cutting edge and further comprising edge protection means extending laterally beyond said cutting edge, said edge protection means cooperating with an adjacent portion of the interior of said tubular member to maintain said cutting edge laterally spaced from the interior of said tubular member.

* * * * *